United States Patent [19]

Wolfrum et al.

[11] Patent Number: 5,002,391
[45] Date of Patent: Mar. 26, 1991

[54] METHOD AND SYSTEM FOR (TRACE) GAS ANALYSIS

[75] Inventors: Jürgen Wolfrum, Obernjesa; Hartmut Neckel, Heidelberg, both of Fed. Rep. of Germany

[73] Assignee: Mutek-Laser und optoelectronische Gerate GmbH, Herrsching, Fed. Rep. of Germany

[21] Appl. No.: 279,214

[22] Filed: Dec. 2, 1988

[30] Foreign Application Priority Data

Dec. 3, 1987 [DE] Fed. Rep. of Germany ....... 3741026

[51] Int. Cl.⁵ .................. G01J 3/427; G01N 21/35
[52] U.S. Cl. .................................. 356/307; 356/320; 356/437; 250/339
[58] Field of Search ............... 356/320, 436, 437, 438, 356/439, 308, 309, 307; 250/339

[56] References Cited

U.S. PATENT DOCUMENTS

| 3,676,004 | 7/1972 | Prugger et al. | 356/315 X |
| 3,820,897 | 6/1974 | Roess | 356/438 X |
| 4,012,145 | 3/1977 | Chabannes et al. | 356/334 X |
| 4,291,988 | 9/1981 | Dixon, Jr. et al. | 356/437 |
| 4,386,854 | 6/1983 | Byer | 356/438 |
| 4,425,648 | 1/1984 | Holly | 356/328 X |
| 4,471,220 | 9/1984 | Perry et al. | 250/339 |

FOREIGN PATENT DOCUMENTS 56-055389 5/1981 Japan .
2127537 4/1984 United Kingdom .

OTHER PUBLICATIONS

Berezovskii et al., *Soviet Journal of Quantum Electronics*, 17:9, 1224–1226, (Sep. 1987).
Moosmuller, *Applied Physics B: Photophysics and Laser Chemistry*, B40:1, 29–33, (1986).
Pokrowsky, *Applied Optics*, 22:4, 2221–2223, (Jul. 1983).
Simhony, et al., *Applied Physics Letters*, 47:12, 1241–1243, (Dec. 1985).

Primary Examiner—Vincent P. McGraw
Attorney, Agent, or Firm—Marshall, O'Toole, Gerstein, Murray & Bicknell

[57] ABSTRACT

What is disclosed is a method and a system for (trace) gas analysis, specifically $NH_3$ analysis in flue gases exhausted from power plants or in industrial waste gases. In this method and system, a laser is reversed between two of its intrinsic resonance lines whereof one wavelength corresponds to an absorption maximum and the other corresponds to an absorption minimum of the gas to be detected. The extinction E and thus the concentration of the gas under analysis is derived from the ratio of the values of intensity attenuation at the two wavelengths.

9 Claims, 8 Drawing Sheets

METHOD AND SYSTEM FOR (TRACE) GAS ANALYSIS

FIELD AND BACKGROUND OF THE INVENTION

The present invention relates to a method and a system for (trace) gas analysis.

It is common knowledge that gases may be identified by their absorption spectrum, with the concentration (K) of the gas being derived from the extinction (E) of a certain wavelength which is characteristic of the gas whose presence is to be detected.

In a known system for flue-gas analysis (applicant's own LORA-1 system) a diode laser is used which can be continuously tuned completely and whose output beam, which is set to a known absorption line of a gas to be detected, is passed through an analyzer while the concentration of the measuring gas in the analyzer is attenuated correspondingly. The magnitude of the concentration of the gas under analysis can be derived from such an attenuation of intensity or such an extinction whenever there is no cross-response to the other gases in the analyzer at the measured wavelength and when, moreover, prior to the beginning of a measuring cycle, a calibration value will have been generated (by introduction of a defined measuring gas concentration). As such a calibration with a gas of a known composition is possible only if the probing section is established within an analyzer cell, flue-gas must be passed through this analyzer cell, e.g. when flue gases emitted from a power plant are to be measured, with the maximum rate of measurement being dependent on the rate of purging the analyzer cell so that it is within the range of several seconds per measurement. Apart from the problem of such comparatively low measuring rate, the known system involves the additional problem that prior to the beginning of the measurement sequence (following the shut-down of the system) calibration is required first, which is a very troublesome and complicated, labor-consuming operation, in addition to the necessity of an analyzer cell with its known drawbacks.

SUMMARY OF THE INVENTION

Proceeding from the afore-described prior art, the present invention is based on the problem of improving a method or a system of the type defined by way of introduction to the effect that with a reduction of the work involved in the measuring operation, a higher measuring rate with a simultaneous increase of the reliability of the measured values can be achieved.

An essential aspect of the invention consists in the formation of a "ratio" between two discrete lines whereof one corresponds to an absorption maximum and the other to an absorption minimum of the gas to be detected. The involved reversing commutation preferably takes place at a comparatively high frequency (e.g. 2,000 cps) with each complete cycle being employed to generate a measured value. This provision allows for in situ measurement, e.g. in the flue of a power plant, without the turbulent flows and eddies prevailing there and involving variations in pressure and temperature (which both take an influence on the absorption characteristics) having an impact. It is therefore not necessary to use optical systems (which are known to be difficult to adjust) to set two laser beams of different wavelengths in a co-linear relationship as one and the same laser generates both wavelengths.

A particular advantage resides in measurement of the intensity of the laser beam before it enters the probing section, preferably simultaneously with a measurement of the intensity of the laser beam leaving the probing section at the delivery end, so that the ratio of the intensities at both wavelengths rather than their magnitudes have to be measured. The ratio of the intensities of the laser beam having passed through the probing sections is then normalized or standardized to the thus established ratio (multiplication with the reciprocal value). With such a system design a stable measurement of the magnitude may be achieved without the requirement that the magnitudes of the laser beam energy must be known.

In a preferred embodiment of the present invention, which produced a specifically surprising effect, a $^{13}CO_2$ laser is used which is reversed from one of its intrinsic lines R(16) to the other R(18) and vice versa by displacement of one of its reflectors or grids, thus providing for a high precision and a high detection sensitivity of the so designed system in the detection of $NH_3$. A response of 1 ppm . m was achieved in a test. The R(16) line of the $^{13}CO_2$ lasers lies in an absorption minimum while the R(18) line of this laser lies in an absorption maximum of ammonia. The application of this system for flue-gas analysis in a power plant permits a measurement directly in the flue-gas passage (flue) as a result of the high efficiency of the laser, so that the result of the measurement (ammonia concentration in the flue gas) may be used to monitor the efficiency of a denitration system or the combustion process. This system involves the specific advantage that there is no cross-response involved as the vapor or even $CO_2$ presents a homogenous absorption in the studied range.

The method according to the present invention moreover permits an analysis of the gas concentration at variable and very high gas temperatures (up to 500° C).

These and other features essential of the present invention can be seen from the dependent claims and the description of preferred embodiments of the invention, which is set out hereinbelow, with all of the described embodiments referring to the detection of the ammonia concentration, particularly in the flue gases exhausted by power plants. It should be emphasized here, however, that the present invention relates also to methods and systems operating on other gas lasers having many different spectrum lines (line ridges or crests), or to any other tunable lasers such as a diode laser. The method is suited for application to general (trace) gas analyses.

BRIEF DESCRIPTION OF THE DRAWINGS

In the following, some preferred embodiments of the present invention will be described with reference to the drawing wherein.

DETAILED DESCRIPTION

Figure 1:
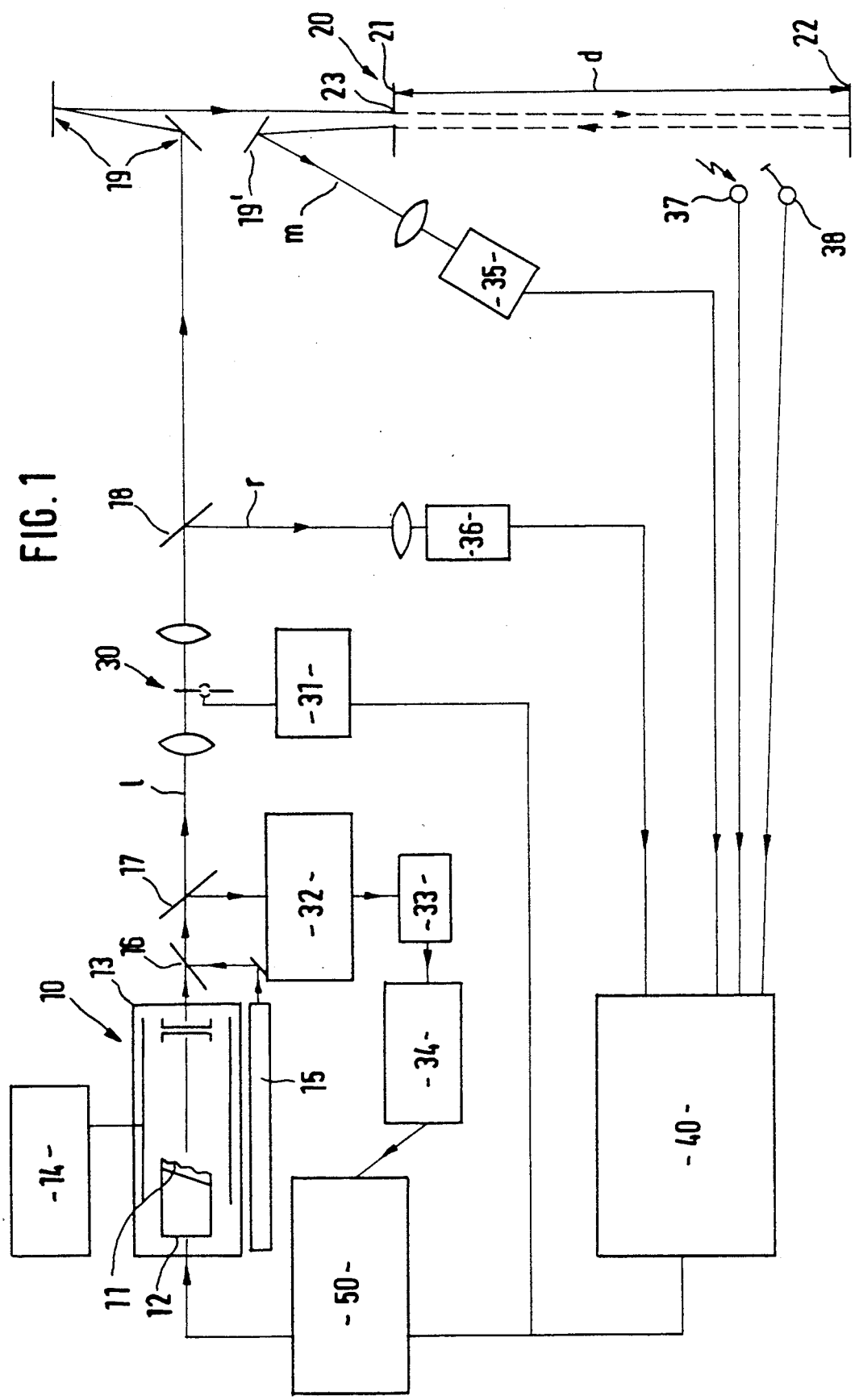
FIG. 1 is a functional diagram of a preferred embodiment of the system according to the present invention.
Figure 2:
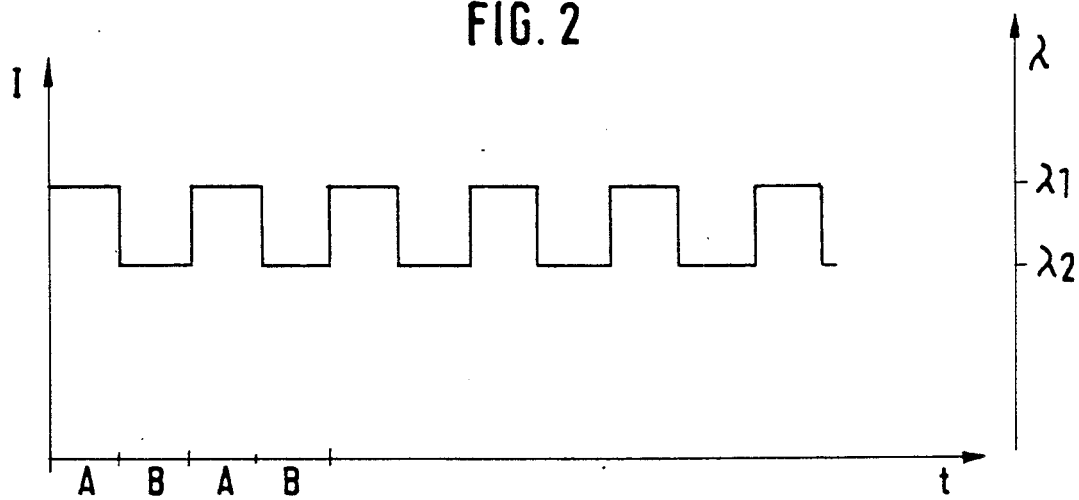
FIGS. 2 to 4 are diagrams explaining the operation of the system in terms of time.

In FIG. 1, reference numeral 10 denotes a laser emitter unit whose housing 13 includes a $^{13}CO_2$ laser. A piezo drive unit may be used to adjust one of the end plates/reflectors/grids 11 of the laser so that resonance may be set to a wavelength typical of the gas used.

The laser is operated at 8° C. approximately, and comprises a power supply 14. The housing 13 includes an isolating jacket maintaining this temperature; this jacket presents one small opening for the laser beam only so as to prevent solidensing phenomena in the optical system. The laser unit as a whole is preferably accomodated in a metal casing which provides for the system shielding against electrical or electromagnetic interference and disturbance.

Moreover, this housing accomodates an HeNe laser for adjustment purposes whose beam may be superimposed to the $CO_2$ laser beam in a co-linear relationship, using a zinc selenide disk 16.

A fraction of the radiation energy of the output laser beam 1 is passed through a partially reflecting end plate 17 and a spectrum analyzer 32 (grid) onto an auxiliary detector 33 measuring the spectrum of the laser beam 1. The output signal issued by the detector 33 is supplied to a stabilizer circuitry 34 employed to control a piezo controller 50 in control of the piezo drive unit. Due to such an arrangement it is possible to set the piezo drive unit 12 in a way that the desired two wavelengths are set with a maximum of precision, while the reflector set may be "detuned" slightly at the same time so as to control the intensity in a way that the output intensity of the laser beam will be at least in the same range of magnitudes for both wavelengths set.

The system is reversed from one wavelength $\lambda_1$ to the other $\lambda_2$ and vice versa at a comparatively high frequency (2,000 cps or Hz approximately) which governs also the synchronization of a chopper 30 through the latter's controller 31. In this system, the controlling functions are so designed that a complete cycle consists of a total of three intervals, with the laser beam 1 being emitted at its first wavelength $\lambda_1$ during the first interval while being emitted at its second wavelength $\lambda_2$ during the second interval, and with the chopper 30 interrupting the laser beam during the third of the three intervals.

An additional, partially reflecting end plate 18 is arranged at the output side of the chopper 30 so as to direct one part of the energy as a reference beam r to a detector 36. The remaining energy of the laser beam 1 is passed via two reflectors 19 and through an aperture 23 in a first end plate 21, impinges on a second end plate 22 at the end of the probing section, and arrives in another detector 35 (after some further steps of reflection between the two end plates 21 and 22) and having passed through the aperture 23 in the first end plate 21 and another reflector 19'. The effective length of the probing section 20 is thus calculated on the basis of the distance d between the two end plates 21 and 22, and as a function of the number of beams reflected to and fro between the end plates.

A temperature detector 37 (such as a radiation pyrometer) and a pressure gauge 38 are provided in or in the vicinity of the probing section 20 (e.g. in the flue itself); the output signals from these sensors and equally the output signals issued by the detectors 35 and 36 are passed to a scoring or evaluation unit 40. The scoring unit 40 is moreover linked up with the piezo controller 50 and the chopper controller 31.

In the embodiment of the invention which is described here, pyroelectrical detectors are used as detector element 35, 36 so that the chopper 30 described here is necessary.

In the following, the operation of the system illustrated in FIG. 1 will be explained in more detail with reference to FIGS. 2 through 7.

The end plate/reflector/grid 11 is so reciprocated by the piezo drive unit 12 that the $CO_2$ laser will reverse between its lines R(16) and R(18) (cf. FIG. 7), i.e. between the two wavelengths $\lambda_1$ and $\lambda_2$ (see FIG. 2), thus following a square course. In this system, the piezo drive unit 12 is so "detuned", e.g. by adjustment of an offset voltage, that the initial intensity (see left coordinate in FIG. 2) for both wavelengths will substantially remain in the same range of magnitudes.

Figure 3:
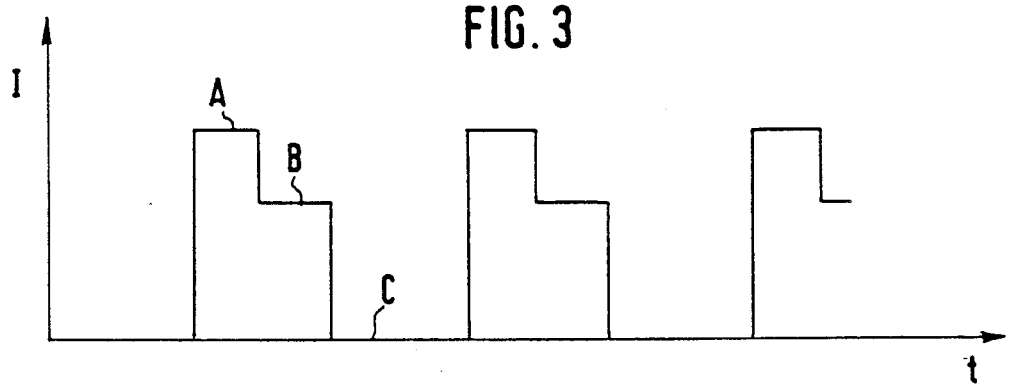
Figure 4:
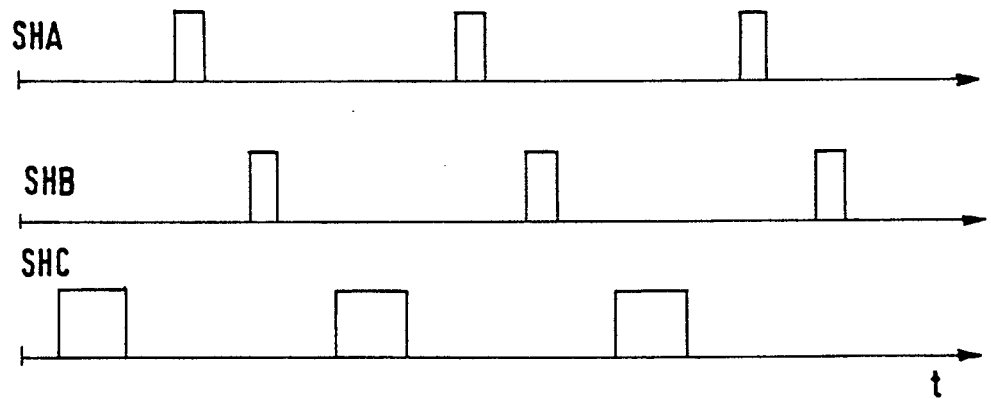
Figure 5:
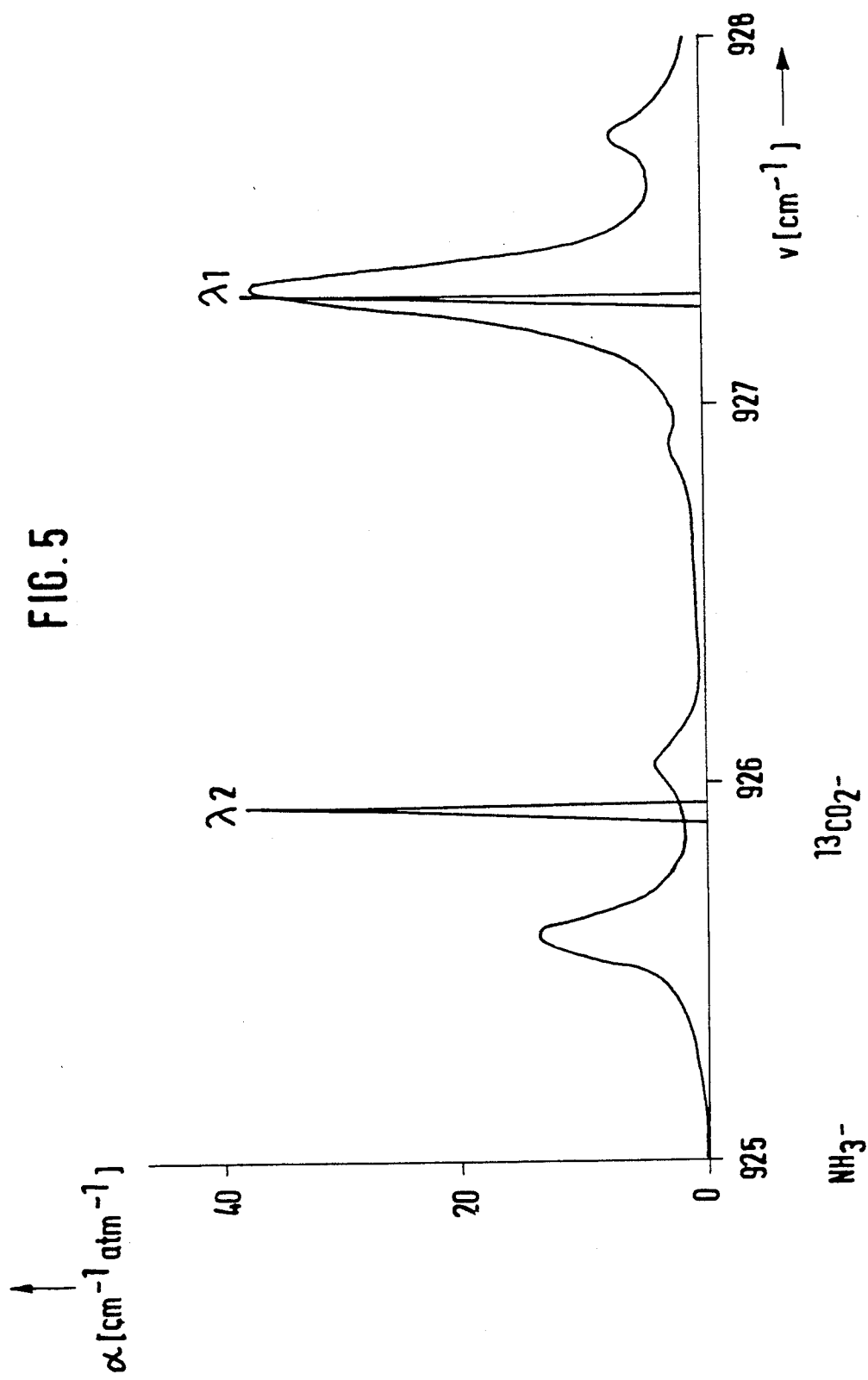
FIG. 5 is a graph explaining the $NH_3$ absorption and the wavelengths used in measurement.
Figure 6:
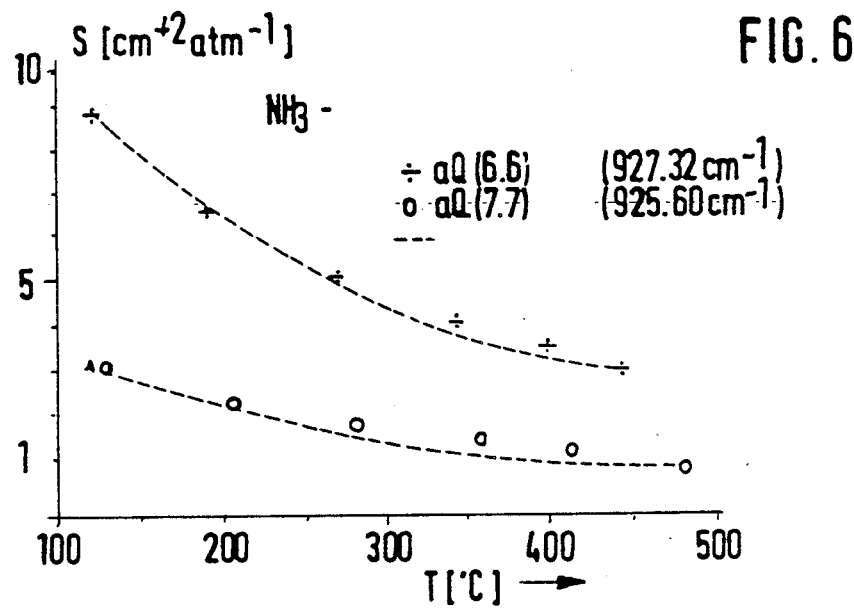
FIG. 6 is a diagram explaining the $NH_3$ line intensities.
Figure 7:
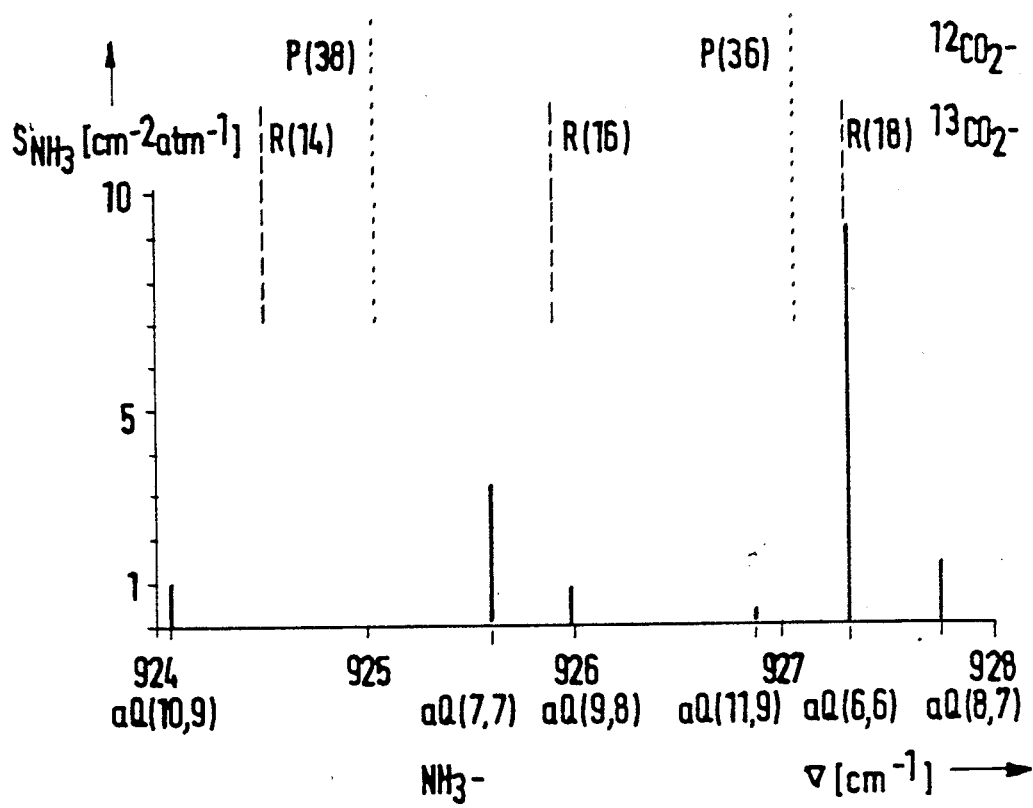
FIG. 7 is a diagram explaining the $NH_3$ absorption lines in contrast to emission lines of different $CO_2$ lasers.

The chopper 30 serves to interrupt the laser beam 1 in synchronism with the reversal of its wavelengths so that the intensity pattern illustrated in FIG. 3 will arise as a function of time, with area A representing a laser beam of wavelength $\lambda_1$, area B denoting a beam of wavelength $\lambda_2$, and area C corresponding to an interval of interruption of the laser beam 1 by the chopper 30. As a result, signals are available at the outputs of the detectors 35 and 36 whose form, as a function of time, corresponds to the form shown in FIG. 3, with the DC mean value of the detector output signals ranging at zero.

Using sample and hold circuits (see FIG. 4) in the scoring unit 40, the output signals from the detectors 35 and 36 are scanned so that after a complete A-C cycle six values are stored altogether: AI, BI, CI (output values A-C from detector 35) and AII, BII, CII (output signals from detector 36). The processed signals A have thus been sensed for wavelength $\lambda_1$ ($NH_3$ absorption maximum) while the values in the B-group are sensed at wavelength $\lambda_2$ (absorption minimum) while the C values represent the optical zero level.

The scoring or evaluation unit 40 now uses these six values to calculate the extinction E, employing the following equation:

$$E = -\log \frac{\left(\dfrac{AI - CI}{BI - CI}\right)}{\left(\dfrac{AII - CII}{BII - CII}\right)}.$$

Gas pressure and temperature in the probing section now being known, the concentration K of the gas under analysis may now be derived directly from these parameters.

Figure 8:
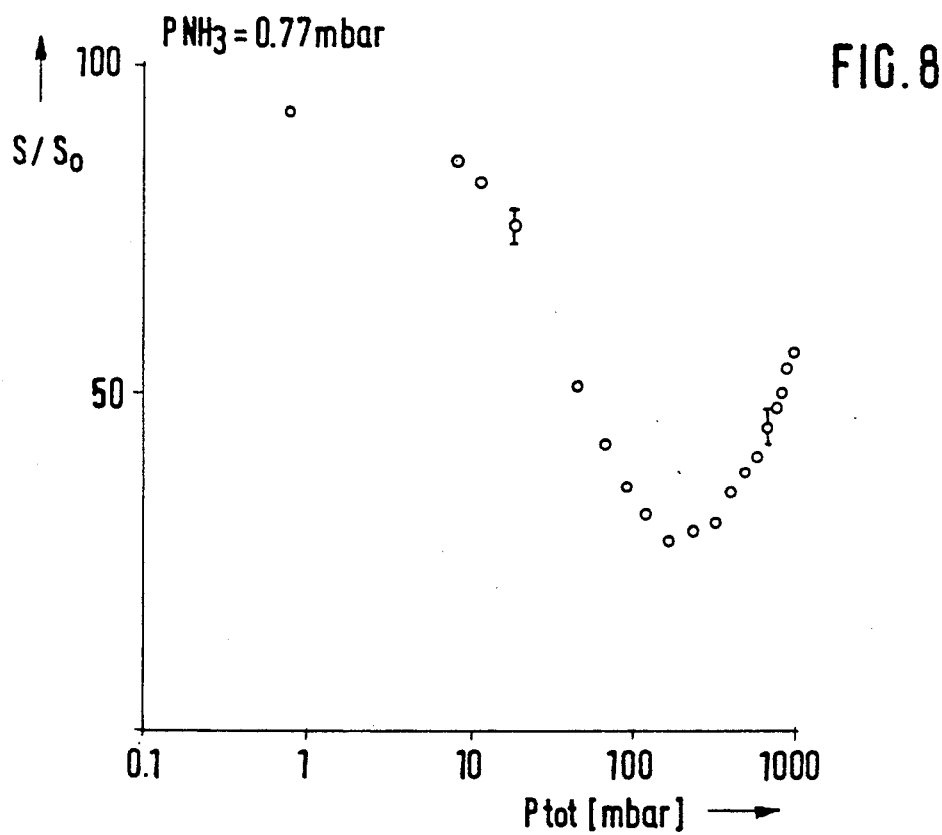
FIG. 8 is a diagram explaining the dependence of the result of measurement on pressure.
Figure 9:
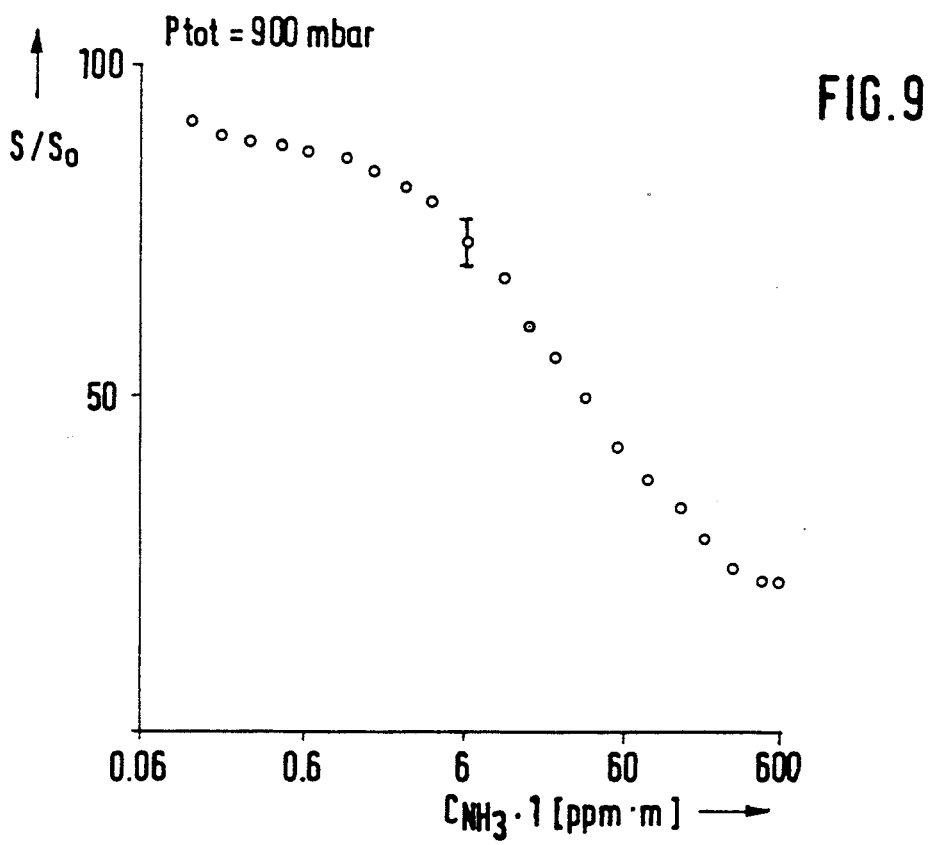
FIG. 9 is a diagram explaining the dependence of the result of measurement on concentration.

As the dependence of absorption from gas pressure and temperature in the probing section is linear only over certain ranges, the measured results need correction; to this end, the scoring unit 40 stores tables of correction factors (see FIGS. 8 and 9) which are then selected as a function of the output signals from sensors 37, 38 and used for correction of the results of measurement.

Figure 10:
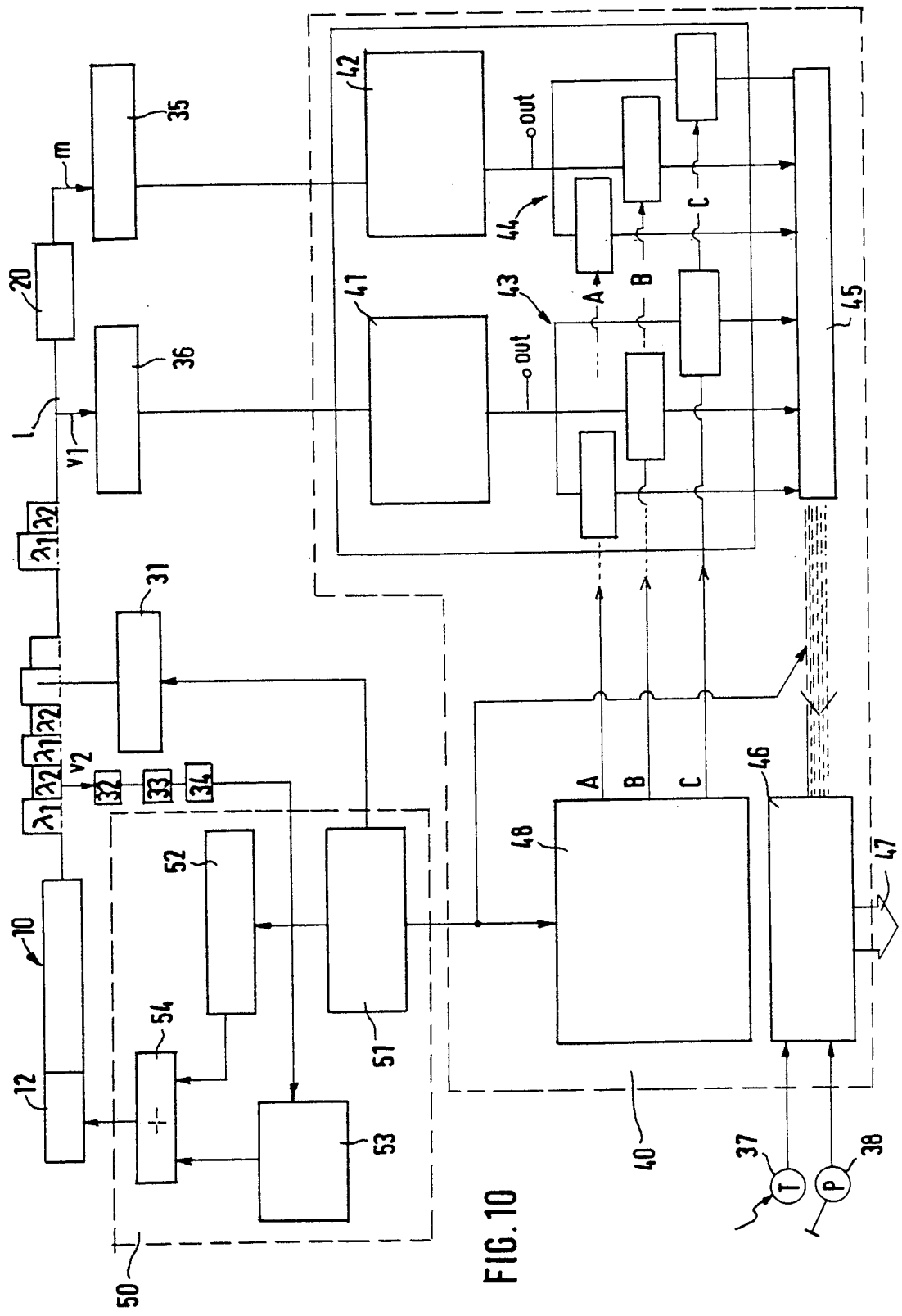
FIG. 10 is a more detailed functional diagram illustrating the evaluation of the results of measurement.

FIG. 10 shows another schematic of the system, which illustrates that the piezo controller 50, in control of the piezo drive unit 12 of the laser emitter unit 10, includes a frequency generator 51 to define the reversing cycle in both commutation between the two wavelengths and interruption of the laser output beam 1. For this reason, the output of the frequency generator 51 is linked up with both the chopper controller 31 and a modulator 52 whose output signal is transferred to an input into an adder-amplifier/driver 54 whose other input receives the output signal from an offset circuit 53. This offset circuit 53 is controlled by the stabilizer circuit 34. Moreover, a clock pulse signal is issued from the frequency generator 51 to an appropriate input of a clocking controller 48 of the scoring unit 40 so as to provide for synchronization of the evaluation circuitry 40.

The clocking controller 48 emits clock pulse signals A, B and C to the sample and hold circuits 43 and 44 which are located at outputs from analog-processing circuits 41 and 42 that process the signals emitted from the pyroelectric detectors 35 and 36. This preliminary processing step includes in particular the decoupling of the offset voltage, with filtering of (HF) noise and amplification of the signals.

The detector values A, B and C stored in the sample and hold circuitry 43 and 44 are digitized by means of an A/D converter 45, and then applied to a computing circuitry 46 (e.g. a mini-computer), together with a clock pulse or trigger signal (from the frequency generator 51). Moreover, the computing circuitry 46 receives (digitized) output signals from the sensing elements 37 and 38 (temperature and pressure in the probing section). The computing circuitry 46 is designed to process, in each cycle and in compliance with the above-defined rule, the signals stored in the sample and hold circuits 43 and 44, to store the results whenever required, and to output them through an output port 47.

Figure 11:
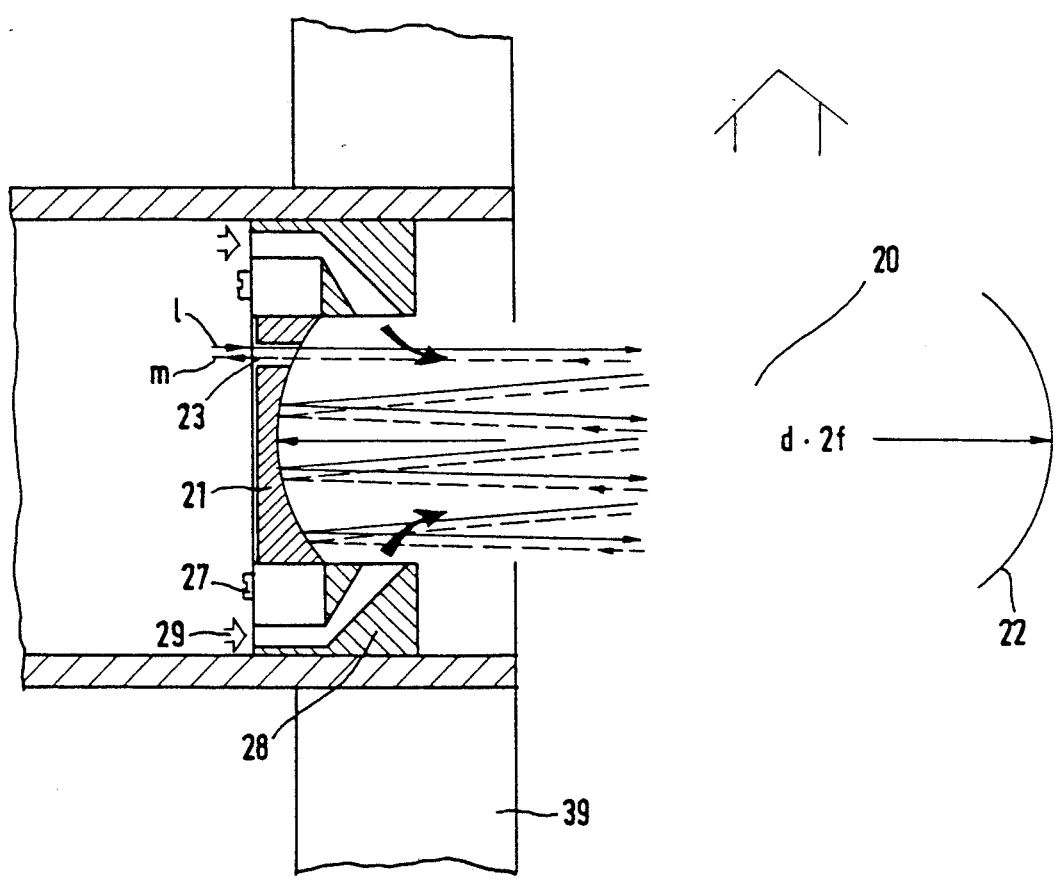
FIG. 11 is a schematic sectional view of a reflector arrangement for the probing section.

The following is a more detailed description of a preferred embodiment of the present invention, in relation to the design of the probing section and with reference to FIG. 11.

As is shown in FIG. 11, the end plates 21 and 22, which have already been described with reference to FIG. 1, are provided in the form of concave reflectors respectively disposed above adjustment means 27 in a casing 28. The casings 28 of both end plates 21 and 22 are installed in opposite walls of a flue 39 so that with an appropriate setting of the end plates, using the adjustment elements 27, a laser beam 1 passing through an aperture 23 in reflector 21 is directed onto the opposite reflector 22, reflected by the latter back onto reflector 21, this reflection cycle being repeated several times until the beam will eventually leave through the aperture 23 in reflector 21 as the measuring beam. In this embodiment, the reflectors 21 and 22 are preferably disposed for adjustment and at a distance d corresponding to the double focal length f of the end plates.

(Annular) purge air passages 29 are provided in the casing 28 for the introduction of purge air (in the direction of the arrow) into the flue in a way that the surfaces of the end plates or reflectors will be protected against contamination, e.g. by solids carried in the flue gases.

Figure 12:
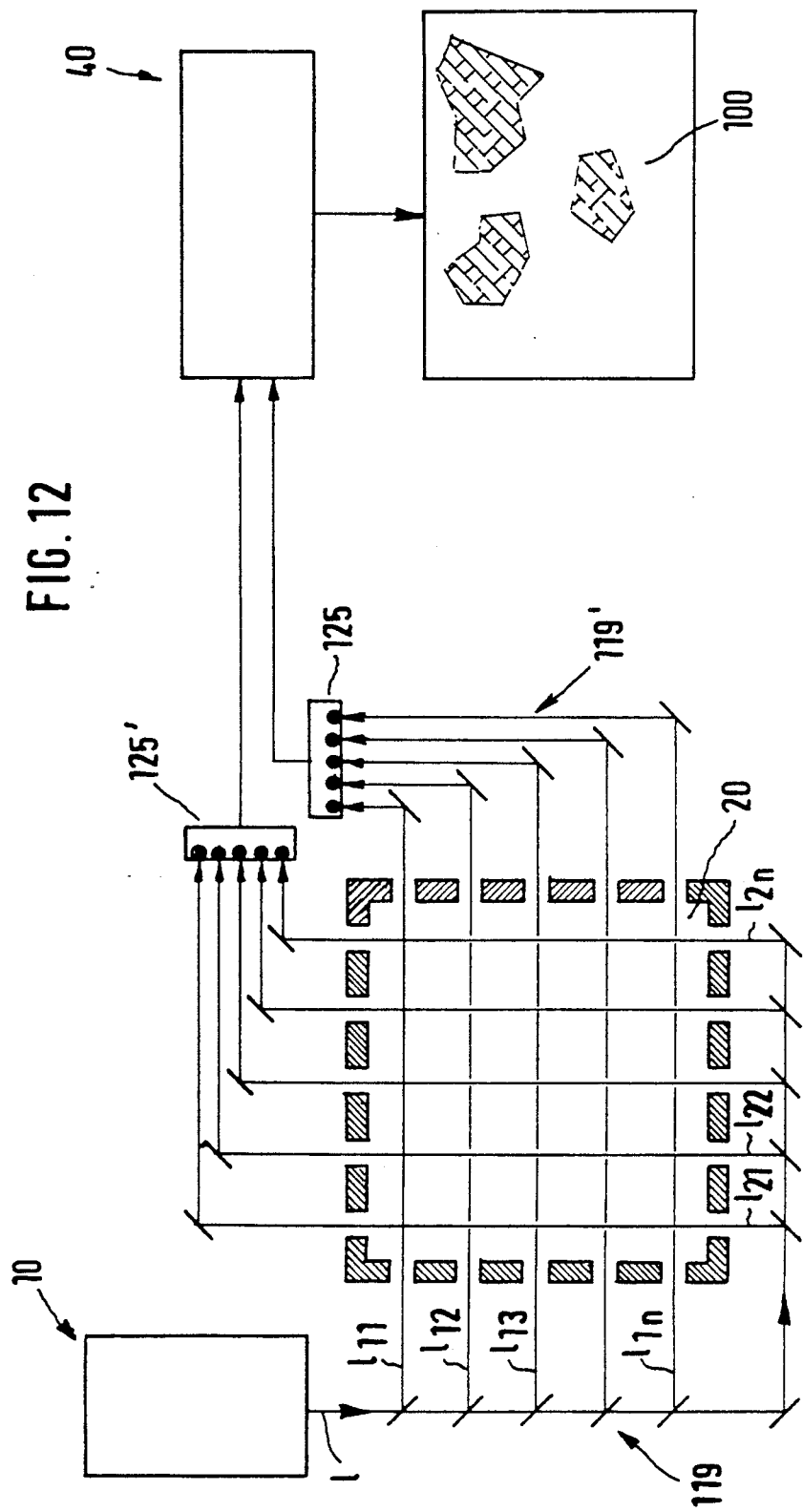
FIG. 12 is a schematic illustration of another preferred embodiment of the present invention, used to establish a two-dimensional concentration profile.

In another preferred embodiment of the present invention, which is illustrated in FIG. 12, the same principle of measurement is applied as that which has been described in detail above already, however with the peculiarity that the laser output beam 1 is split by reflector sets 119, 119' into a matrix-type array of individual measuring beams which, having passed through the probing sections 20, are each adjusted to groups of detectors 125, 125' whose output signals are as well supplied to a scoring or evaluating unit 40. The scoring unit 40 uses the measured values to generate a tomogram-type representation suited for output in the form of a hard copy 100 presenting a two-dimensional concentration profile over the flue cross-section.

The components and devices already explained with reference to FIGS. 1 through 10 (analyzer, chopper, etc.) are provided, of course, in this system as well.

It should be emphasized here again that the invention does not only relate to a $^{13}CO_2$ laser but to any laser in general whose wavelength may be tuned to at least two values, thus covering laser diodes as well.

The application of the aforedescribed present invention to the analysis of the ammonia concentration in flue gases provides for a surprisingly precise and yet comparatively simple in situ analysis of the flue gases. Such an application involves a substantial advantage insofar as each measured value may be derived from three discrete values obtained in very short successive intervals, which will, in its turn, result in the fact that turbulent flows or eddies in the flue gas or even vibrations (such as vibrations in the building) occurring at the location of installation will not have any impact on the result of measurement as the rate at which pressure and flow in such eddies or the upper frequency limit of vibrations of the building vary, is lower than the rate of measurement in the system. With operation on other wavelengths of the laser beam or with different types of measuring gas, it is possible in the present method or system, of course, to detect other gases by way of analogy. In any case, however, a $CO_2$ laser presents a very high efficiency so that particularly long probing sections may be designed which will entail a high sensitivity in detection.

We claim:

1. A system for monitoring exhaust gases comprising a laser unit comprising a $CO_2$ laser for generating a laser beam;

first optical means for guiding the laser beam into a probing section containing exhaust gas to be monitored;

at least one measuring unit comprising a pyroelectric detector for measuring the intensity of said laser beam and providing corresponding laser beam intensity output signals;

second optical means for guiding the laser beam leaving said probing section to said measuring unit;

tuning means comprising a piezoelectric drive unit for adjusting said $CO_2$ laser either to a first wavelength ($\lambda 1$) corresponding to an absorption maximum of a gas contained in said exhaust gas or to a second wavelength ($\lambda 2$) corresponding to an absorption minimum of said gas;

a controller for controlling said tuning means in accordance with first control signals;

a chopper for alternatively passing through or stopping down said laser beam in accordance with second control signals;

sample and hold means for sampling and holding said laser beam intensity output signals of said at least one measuring unit in accordance with third control signals;

a scoring circuit generating said first, second and third control signals and for correcting, processing, and displaying said laser beam intensity output signals from said measuring unit sampled and held by said sample and hold means;

measuring means for measuring temperature and pressure of said exhaust gas;

storage means for storing a table of correction factors as a function of gas temperature and gas pressure;

means for reading said correction factors from said table of correction factors in accordance with said measured temperature and pressure and for feeding said correction factors to said scoring circuitry;

wherein said first, second, and third control signals are generated and synchronized such that said piezoelectric drive unit cylically adjusts said $CO_2$ laser for reversing the wavelength of said laser beam between said first and said second wavelength at a first frequency in excess of 1000 cps, said chopper alternatively passes through and stops down said laser beam at a second frequency the value thereof being half of said first frequency such that one cycle of wavelength reversion occurs during passing through and one cycle of wavelength reversion occurs during stopping down of said laser beam, and during passing through of said laser beam said sample and hold means takes a sample of said laser beam intensity output signals at a defined time interval after reversing the wavelength and, during stopping down of said laser beam, takes a sample at a defined time interval after stopping down of said laser beam.

2. A system according to claim 1 in which said scoring circuit includes intensity measuring means for measuring the intensity of the laser beam wherein said scoring circuit being adapted to normalize an intensity ratio (AI/BI) of the laser beam after passage through said probing section to an intensity ratio (AII/BII) prior to the passage through said probing section.

3. A system according to claim 1 in which said piezoelectric drive unit is provided with an offset adjustment means being adapted to set the initial intensity of said laser beam independently of the reversing of said laser beam from one wavelength to the other.

4. A system according to claim 1 including a laser beam analyzer unit for determining an emission spectrum of said laser beam, a stabilizing circuit for receiving output signals of said analyzer unit, a control/driver circuit receiving output signals from said stabilizing circuit and being connected to said piezoelectric drive unit for feedback controlling and monitoring of emission wavelengths and intensities of said laser beam.

5. A system according to claim 1 including an additional laser emitting light in a visible range and means for superimposing said light in co-linearity with said laser beam for adjusting and balancing of the system.

6. A system according to claim 1 in which said probing section includes a pair of reflectors in mutually opposite relationship such that a beam directed onto one of said reflectors will be reflected to and fro several times between said reflectors, thus passing through said probing section, until it is diverted out of the probing section and coupled to said measuring unit.

7. A system according to claim 6 in which said reflectors include concave reflectors having double focal lengths (f) corresponding to the length (d) of said probing section.

8. A system according to claim 1 in which said first and second optical means are positioned with respect to said probing system for defining a cross-sectional region of a passage through which said exhaust gas passes such that a plurality of laser beams passes therethrough in the form of a matrix, wherein said system comprises a pair of groups of measuring units coupled to said scoring circuit for measuring the intensity of said output beams, said scoring circuit being adapted for recording and displaying a two-dimensional profile of measured values.

9. A system according to claim 1 in which said $CO_2$ laser is a $^{13}CO_2$ laser for measuring ammonia concentration.

* * * * *